(12) United States Patent
Shennib

(10) Patent No.: US 7,016,504 B1
(45) Date of Patent: Mar. 21, 2006

(54) PERSONAL HEARING EVALUATOR

(75) Inventor: Adnan Shennib, Fremont, CA (US)

(73) Assignee: Insonus Medical, Inc., Hayward, CA (US)

( * ) Notice: Subject to any disclaimer, the term of this patent is extended or adjusted under 35 U.S.C. 154(b) by 0 days.

(21) Appl. No.: 09/400,151

(22) Filed: Sep. 21, 1999

(51) Int. Cl.
H04R 29/00 (2006.01)

(52) U.S. Cl. ............................ 381/60; 73/585; 600/559

(58) Field of Classification Search ............... 381/60, 381/68, 315, 320, 56, 26; 73/585; 600/559, 600/340; 340/686.1, 825.36; 607/57, 136, 607/137
See application file for complete search history.

(56) References Cited

U.S. PATENT DOCUMENTS

| | | | |
|---|---|---|---|
| 3,594,514 A | | 7/1971 | Wingrove |
| 3,764,748 A | | 10/1973 | Branch et al. |
| 3,870,832 A | | 3/1975 | Fredrickson |
| 3,882,285 A | | 5/1975 | Nunley et al. |
| 3,905,131 A | * | 9/1975 | Feezor et al. ............... 434/221 |
| 4,505,329 A | | 3/1985 | Nguyen-Thanh |
| 4,548,082 A | * | 10/1985 | Engebretson et al. ......... 73/585 |
| 4,615,007 A | * | 9/1986 | King et al. ................. 364/415 |
| 4,628,907 A | | 12/1986 | Epley |
| 4,756,312 A | | 7/1988 | Epley |
| 4,776,322 A | | 10/1988 | Hough et al. |
| 4,817,607 A | | 4/1989 | Tatge |
| 4,840,178 A | | 6/1989 | Heide et al. |
| 4,918,737 A | * | 4/1990 | Luethi ....................... 381/68.4 |
| 4,957,478 A | | 9/1990 | Maniglia |
| 4,964,304 A | * | 10/1990 | Eckstein ....................... 73/585 |
| 5,012,520 A | * | 4/1991 | Steeger ....................... 381/68 |
| 5,015,224 A | | 5/1991 | Maniglia |
| 5,015,225 A | | 5/1991 | Hough et al. |
| 5,081,441 A | * | 1/1992 | Chojar ....................... 340/384.7 |
| 5,163,957 A | | 11/1992 | Sadé et al. |
| 5,197,332 A | * | 3/1993 | Shennib ....................... 73/585 |
| 5,210,803 A | * | 5/1993 | Martin et al. ................. 381/68 |
| 5,220,918 A | | 6/1993 | Heide et al. |
| 5,259,032 A | | 11/1993 | Perkins et al. |
| 5,282,858 A | | 2/1994 | Bisch et al. |
| 5,303,306 A | * | 4/1994 | Brillhart et al. ............. 381/68 |
| 5,338,287 A | | 8/1994 | Miller et al. |
| 5,420,930 A | * | 5/1995 | Shugart, III ............... 381/68.6 |
| 5,425,104 A | * | 6/1995 | Shennib ....................... 381/68 |

(Continued)

OTHER PUBLICATIONS

Chasin, Marshall, *CIC Handbook*, Singular Publishing Group, Inc. (1997), pp. 12-14, 17-18, 27-28, 44, 56-58, and 65-66.

(Continued)

*Primary Examiner*—Duc Nguyen
*Assistant Examiner*—Lun-See Lao
(74) *Attorney, Agent, or Firm*—Townsend and Townsend and Crew, LLP

(57) ABSTRACT

A hand-held device includes an audio transducer (i.e., speaker) for delivering acoustic test stimuli to a test subject within the direct sound field range of the device. The device accurately delivers multi-level and multi-frequency test stimuli for the subjective response by the test subject holding the device. An ultrasonic position sensor within the device determines the position of the device with respect to the head or a portion of interest of the head of the test subject while the device is being held. The acoustic test stimuli are controlled and regulated based on the position of the device with respect to the test subject so that accurate levels of test stimuli are presented only when the device is within a proper range and irrespective of its exact position with respect to the test subject's head.

74 Claims, 9 Drawing Sheets

U.S. PATENT DOCUMENTS

| | | | |
|---|---|---|---|
| 5,428,998 A * | 7/1995 | Downs | 73/585 |
| 5,456,654 A | 10/1995 | Ball | |
| 5,531,787 A | 7/1996 | Lesinski et al. | |
| 5,554,096 A | 9/1996 | Ball | |
| 5,615,229 A * | 3/1997 | Sharma et al. | 375/259 |
| 5,624,376 A | 4/1997 | Ball et al. | |
| 5,645,074 A * | 7/1997 | Shennib et al. | 600/559 |
| 5,654,530 A | 8/1997 | Sauer et al. | |
| 5,682,020 A | 10/1997 | Oliveira | |
| 5,701,348 A | 12/1997 | Shennib et al. | |
| 5,721,783 A * | 2/1998 | Anderson | 381/68.6 |
| 5,833,626 A | 11/1998 | Leysieffer | |
| 6,302,438 B1 * | 10/2001 | Stopper et al. | 280/735 |
| 6,304,179 B1 * | 10/2001 | Lotito et al. | 340/545.3 |
| 6,366,863 B1 * | 4/2002 | Bye et al. | 702/57 |
| 6,408,081 B1 | 6/2002 | Boesen | |
| 6,620,110 B1 | 9/2003 | Schmid | |
| 6,643,378 B1 | 11/2003 | Schumaier | |
| 6,648,813 B1 | 11/2003 | Zilberman et al. | |
| 6,658,126 B1 | 12/2003 | Stern | |

OTHER PUBLICATIONS

Oliveira, Robert J., and Navarro, Richard, "The Wax Problem: Two New Approaches," *The Hearing Journal* (Aug. 1993) vol. 46, No. 8, pp. 41-46.

* cited by examiner

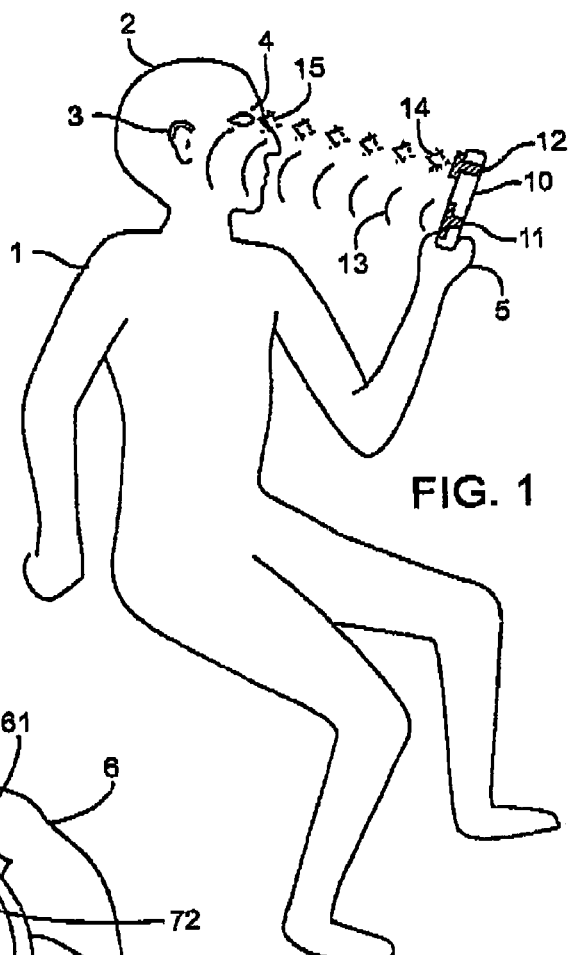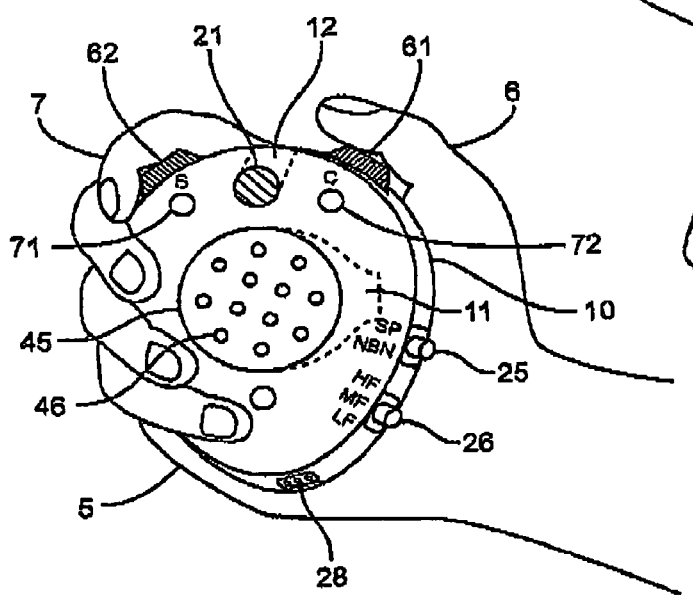
FIG. 1
FIG. 2

PERSONAL HEARING EVALUATOR

BACKGROUND OF THE INVENTION

A. Technical Field

The present invention relates generally to air-conduction hearing evaluation, and more particularly, to portable hand-held hearing testing and hearing aid fitting.

B. Description of the Prior Art

Air-conduction hearing evaluation involves the presentation of airborne sounds (test stimuli) to the ears of a test subject. The evaluation may involve threshold measurements whereby the threshold of hearing is determined at various frequencies, or suprathreshold measurements whereby loudness perceptions above threshold are determined. Suprathreshold testing include most comfortable loudness (MCL), uncomfortable loudness (UCL) and dynamic range measurements. A variety of test stimuli types are employed in audiological testing including pure tones, speech, and a variety of noise-based signals.

Test stimuli in air-conduction testing are emitted from a speaker to travel in air and ultimately reaching the eardrum. A speaker is typically positioned directly on or within the ear as in the case of circumaural earphones (headphones) and insert earphones. Alternatively, in sound field testing, a speaker is placed at a distance from the ear of the test subject in a test room (See American National Standard, specification for Audiometry, ANSI S3.6-1996).

Sound field evaluation generally involves bulky instrumentation, complex calibration procedures and require specialized test rooms. Furthermore, precise positioning of the subject with respect to a speaker is necessary in order to minimize errors in the intensity level of the sound at the ear. These errors are also caused by reverberations commonly found in test rooms (see Sandlin, R, Handbook of Hearing and Amplification, Ch. 6. pp 147–164, Singular Publishing group, 1995). FIGS. 6–3 of Sandlin, for example, demonstrate how large the variability of pure tone sound field measurement can be for small changes in distance between the subject and the speaker.

In standard sound field audiometry, the subject is typically placed approximately at 1 meter (m) from the speaker. Unfortunately, the reverberant component of sound at 1 millimeter (mm) is significant as shown in FIGS. 6–2 of Sandlin. The use of anechoic test rooms to eliminate reverberant sounds is extremely expensive and thus not employed in standard audiological test setups.

To minimize the effect of reverberant sounds, the subject should be positioned within the direct field of sound, which is typically within 70 centimeters (cm) from speaker. This causes the direct sound in the direct field to be dominant with respect to reverberant sound reflected from nearby objects in the room (i.e., walls, ceiling, floor, equipment, etc.). However, maintaining a precise seating arrangement within 70 cm of a speaker presents many challenges related to subject movement, discomfort, and even claustrophobia.

The utilization of probe tube microphone system to calibrate and regulate presentation levels has been widely used for various hearing evaluations (for example, see pp. 192–204 in Sandlin). However, probe tube microphone instrumentation requires careful positioning of the probe tube for each hearing evaluation step performed. Furthermore, the use of microphone probe tube systems adds considerable cost and complexity for the evaluation procedure, not to mention the inconvenience of attaching and maintaining a probe tube and its cabling for both the subject and the clinician.

In headphone audiometry (TDH-39 type for example), the distance between the test ear and the speaker is relatively stable thus alleviating the problem of speaker-subject positioning encountered in sound field audiometry. However, the headphone must be fitted in a sealing manner in order to minimize errors due to sound leakages that may occur at the headphone-ear contact area. Insert earphones (ER-3A type for example) also require a good sealing fit when inserted within the ear canal. Headphone and insert earphones can be uncomfortable and cumbersome for many individuals. Furthermore, headphone and insert earphones are particularly problematic for aided evaluation (with a hearing aid placed in the ear) because they generally interfere, physically and acoustically, with the proper function of a worn hearing device. Therefore, headphone and insert earphones are generally excluded from aided evaluation. Other problems associated with headphones and insert earphones include inaccuracies due to individual ear size variability and cabling interference and damage.

Portable and hand-held hearing evaluation is advantageous for conducting hearing testing outside the standard calibrated audiological setups. However, due to the relatively large errors associated with outside room acoustics, calibration, speaker-subject positioning and ambient background noise, portable and hand-held instruments tend to be limited to basic screening evaluation, requiring follow up testing in a proper audiological setup.

Review of State-of the-Art in Related Hearing Device Technology

Heller, J., in U.S. Pat. No. 4,567,881 describes a combination otoscope and audiometer for performing audiometric testing during otoscopic examination. Since the testing is performed while the tip of the otoscope is inserted in the ear canal, it is obviously not intended for aided evaluation whereby a hearing aid is worn in the ear canal. Furthermore, an otoscope is intended for use by a professional thus not suitable as a personal hearing evaluator.

Shennib, A. in U.S. Pat. No. 5,197,332 describes a headset hearing tester which is worn on the head for positioning a speaker portion directly on the ear. As previously observed, headphone type audiometry not only interferes with the proper function of most hearing aids when worn, but is also bulky and uncomfortable for many users.

Chojar in U.S. Pat. No. 5,081,441 discloses a hand-held tone generator for generating an audible tone as a test for equalizing binaural hearing aids. Chojar's device is limited to producing a single tone at single level, thus clearly not suitable for performing audiometric measurements. In fact, it is merely concerned with ensuring a balanced binaural aided hearing.

Downs, M., in U.S. Pat. No. 5,291,785 describe a hand-held portable device for testing infants for hearing defects. The device produces a low intensity sound for eliciting a response and a high intensity sound for eliciting reflex from the infant. Although designed to produce multi-level acoustic stimuli, the device is essentially a screening device for infants, thus not concerned with presenting accurate stimulus levels at multiple frequencies, nor concerned with aided evaluation. Furthermore, the device is clearly not designed for self-testing.

Posen et. al., in U.S. Pat. No. 5,732,396 disclose a hand-held screening device for generating various acoustic stimuli at a distance set by a physical spacer incorporated into the screening device. The spacer makes direct contact with the ear area for positioning the speaker at 1½ to 2¼ inches form the ear. The screening device, with a spacer incorporated within, has the advantage of providing a predetermined distance between the speaker and the test ear. However, the direct contact of the device to the ear area is not only awkward for audiometric testing, but is also difficult to operate by an individual of limited dexterity in self-testing scenarios. Furthermore, testing involving both ears simultaneously (binaural mode) is not possible with such a device.

There are numerous situations whereby it is desirable to provide a hand-held hearing evaluator with accurate multi-level test sounds. It is also desirable to provide a miniature instrument with means for self-administered testing without resorting to an expensive test performed by a hearing professional. In another situation, it is desirable to have a personal hearing evaluator to regularly verify the function of a worn hearing device. This is important since hearing aids are notorious for being subject to frequent damage and deterioration.

Therefore, it is a principal objective of the present invention to provide a hand-held hearing evaluation device for presenting multi-level and multi-frequency stimuli.

Another objective is to provide contactless means to properly position a speaker with respect to a test individual for accurate presentation of test stimuli.

A further objective is to provide a hearing evaluation device with means to automatically calibrate the level of acoustic stimuli presented.

A further objective is to provide an easy to use hand-held hearing evaluator suitable for self-administration by a test subject in either aided or unaided conditions.

SUMMARY OF THE INVENTION

The invention provides a hand-held device comprising an audio transducer (i.e., speaker) for presenting acoustic test stimuli to a test subject within the direct sound field range of the device. The device delivers accurate multi-level and multi-frequency test stimuli for subjective response by the test subject holding the device. The battery-operated device is suitable for various hearing evaluation modes including aided (i.e., with a hearing aid worn) and unaided conditions.

In a preferred embodiment, the invention comprises an ultrasonic position sensor for measuring the position of the device with respect to the head of the test subject holding the hand held device. The distance is computed by measuring the latent period between the transmitted ultrasonic signal and the measured ultrasonic response reflected by the head or the ear. The acoustic test stimuli produced by the speaker are controlled and regulated based on the position of the device with respect to the test individual. Thus, the accurate levels of test stimuli are presented only upon the proper positioning of the device and irrespective of the exact position of the device. This eliminates position and movement-related errors commonly experienced in conventional sound field audiometry. Furthermore, the test subject or a test operator is automatically alerted whenever the device is incorrectly positioned during a test.

In an embodiment of the invention, the hand-held device is connected to an auxiliary instrument (e.g., a computer or a microprocessor-based audiometer) for remotely controlling the device and for registering audible responses via a response switch provided on the invented device. In such embodiments, a test operator can select an acoustic test stimulus from a broader range of test stimuli. Thus, various threshold and supra-threshold tests are presented and responses are automatically registered by the auxiliary instrument.

In the preferred embodiment, the hand-held device is provided with at least two keys for selecting and presenting at least two stimulus levels. For example, the two keys may be an "S" key for presenting Soft level sound and a "C" key for presenting Comfortable level sound. The keys can be used by a test subject to routinely check the proper function of an in-situ (worn in the ear) hearing device. In another stand-alone embodiment, the hand-held device is used as an audiometric tool to assess hearing ability and specifically the need for a hearing aid use.

In the preferred embodiment, the device also provides switches for selecting one of at least two signal types such as Noise and Speech signals, and for selecting at least two frequency bands such as Low and High frequency bands. The combination of switches and key selections leads to a broad yet manageable range of test options, such as Soft level Highfrequency Speech or Comfortable level Low frequency Noise.

The device may be designed and configured for dual mode configurations by first being connected to an auxiliary instrument for performing relatively complex aided and unaided audiometric evaluation in the presence of a hearing professional, and subsequently as a personal evaluator for simple verification of hearing acuity and hearing aid function.

The device may be used for either binaural or monaural hearing evaluations. In binaural tests, the speaker of the device is oriented facing the forehead at a distance between 30–60 cm, depending on the individual's arm length. Although miniature and employing a miniature audio transducer, the device can produce high relatively intensity levels reaching 90 decibels (dB) sound pressure level (SPL) and more when positioned close to an ear (i.e., within few centimeters) in a monaural test mode.

BRIEF DESCRIPTION OF THE DRAWINGS

The above and other objectives, features, aspects and attendant advantages of the invention will become further apparent from a consideration of the following detailed description of the presently contemplated best mode of practicing the invention, with reference to certain preferred embodiments and methods thereof, in conjunction with the accompanying drawings, in which:

FIG. 1 is a view of a preferred embodiment of the invention showing a hand held hearing evaluation device containing a speaker and position sensor system, both oriented towards the head of the user;

FIG. 2 is a more detailed perspective view of the hearing evaluation device of FIG. 1 being held in hand by a user;

DETAILED DESCRIPTION OF THE PREFERRED EMBODIMENTS AND METHODS

Figure 3:
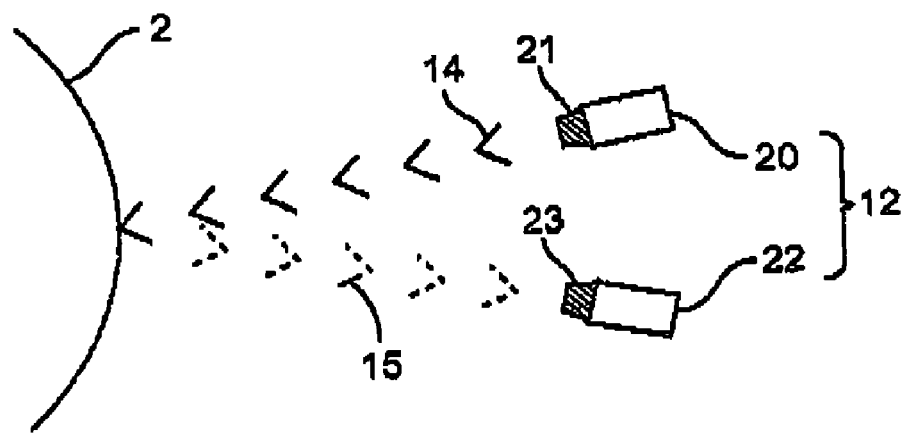
FIG. 3 is a view of a dual-transducer position sensor for the embodiment of FIG. 1, having a transmitting ultrasonic transducer and a reception ultrasonic transducer.

The present invention, shown in FIGS. 1–13, provides a personal hearing evaluation device 10 for accurately presenting multi-level acoustic test stimuli (sounds) to an individual via an audio transducer (i.e., speaker) 11 incorporated within the housing of the device. The invented device 10, as shown in FIGS. 1 and 2, is designed for holding by hand and for directing sound 13 from its speaker 11 towards an ear 3 of a user 1 in a contactless manner but within the direct sound field range of the speaker. In the preferred embodiments, shown in FIGS. 1–11, the device 10 comprises a position sensor 12 for automatically measuring the position of the device 10 with respect to the user's head 4, or a part thereof of interest, depending on the test mode as described below. The device 10 also comprises keys (switches, e.g., 61 and 62, FIG. 2) for selecting at least two levels of sound 13, presented in the direction of an ear (monaural mode, FIGS. 8 and 9) or both ears (binaural mode, FIGS. 6 and 7).

The position sensor 12 incorporated in the preferred embodiment of the invented device produces incidence wave 14 (solid arrows) which partially bounces off the head, or a part thereof (i.e., nose, forehead, chin, ear, etc.), and becomes a reflected wave 15 (dashed arrows) for reception by the position sensor 12. The position sensor 12 in the preferred embodiment comprises one or more ultrasonic transducers. FIG. 3 shows a position sensor 12 employing a pair of ultrasonic transducers. The first transducer is a transmitter 20 for emitting incident wave 14, and second transducer is a receiver 22, for receiving the reflected wave 15 bouncing off the head or a part thereof. The transmitter 20 and receiver 22 transducers further employ directional filters, 21 and 23, respectively, for appropriately directing the incident wave 14 and receiving reflected wave 15. These filters improve the reception and directionality of the position sensing process for ensuring proper positioning of the device with the respect to the individual.

Figure 4:
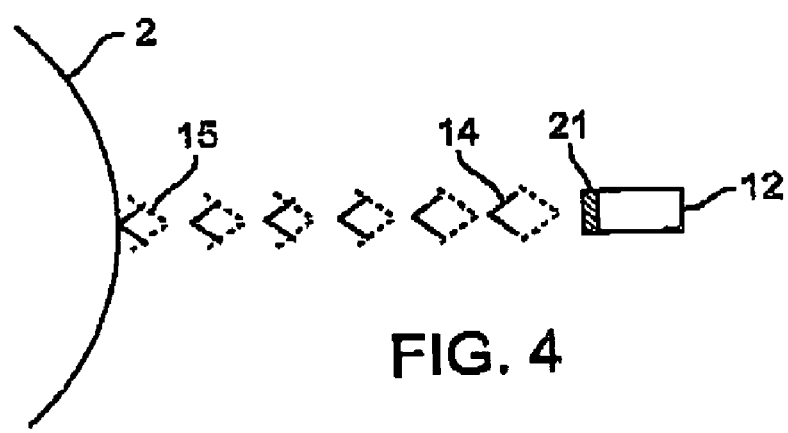
FIG. 4 is a view of a single-transducer position sensor which is preferred for the embodiment of FIG. 1, having a unitary transducer for both transmitting and reception of ultrasonic signals.

In a preferred embodiment of the position sensor, shown in FIG. 4, a unitary ultrasonic transducer 12 (for example, piezoelectric transducer model ITC-9073 manufactured by International Transducer Technology, Inc.) is employed both for transmitting incident wave 14 and for receiving reflected wave 15. This unitary transducer design consumes less space and thus is more suited for the miniature battery-operated design of the hearing evaluation device of the invention.

Figure 5:
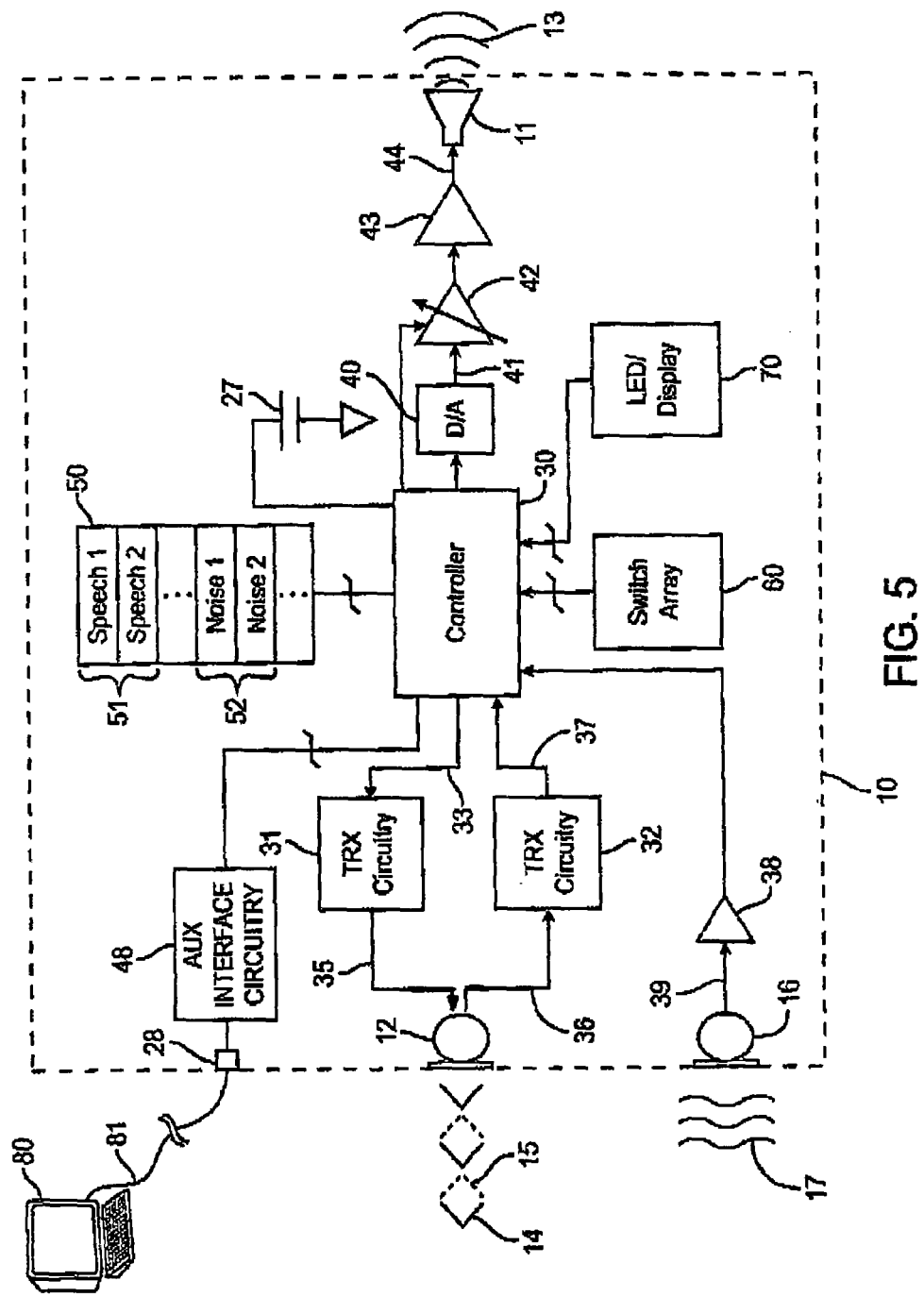
FIG. 5 is a block diagram of the major components within the presently preferred embodiment of the hearing evaluation device.
Figure 11:
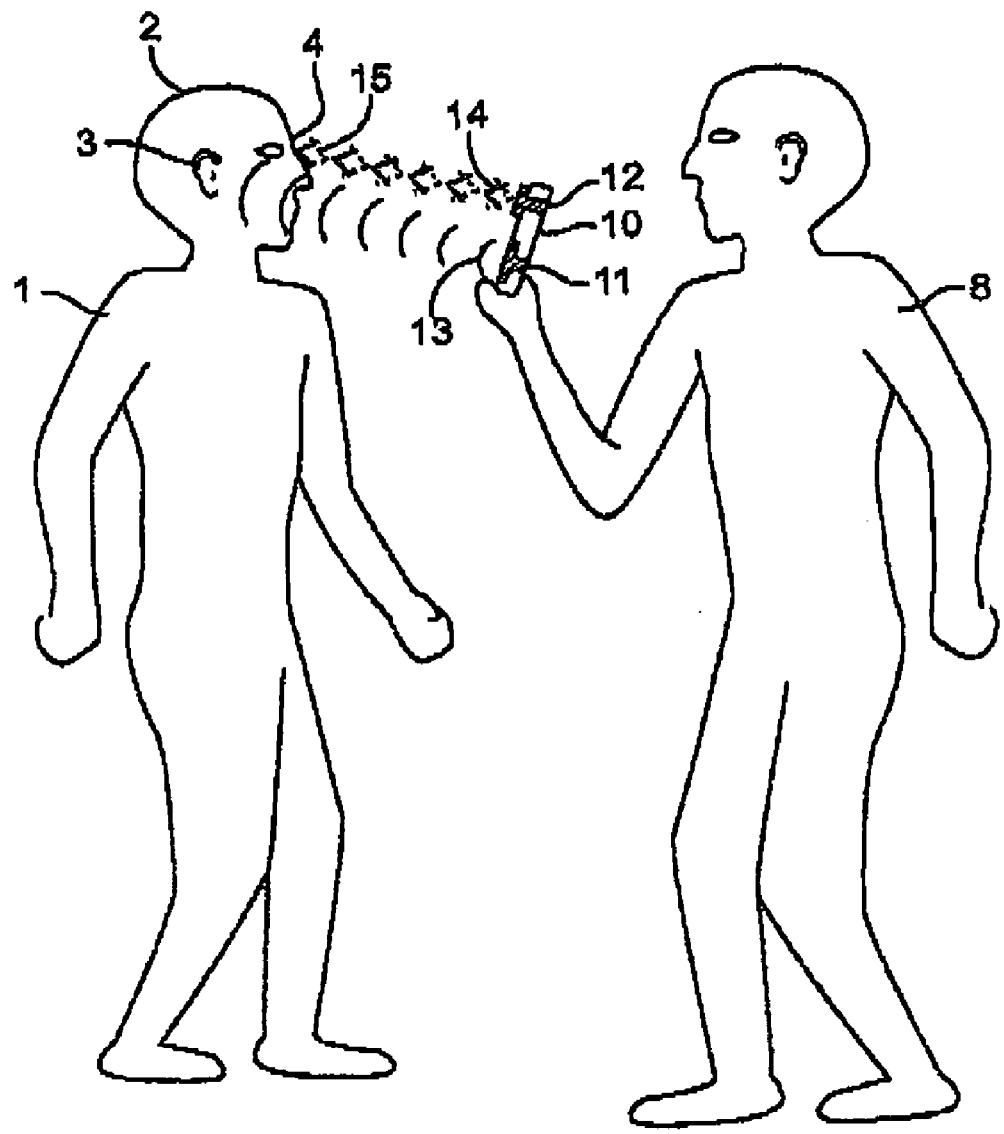
FIG. 11 is a view of the hearing evaluation device held by a test operator directing the speaker at a test subject.
Figure 12:
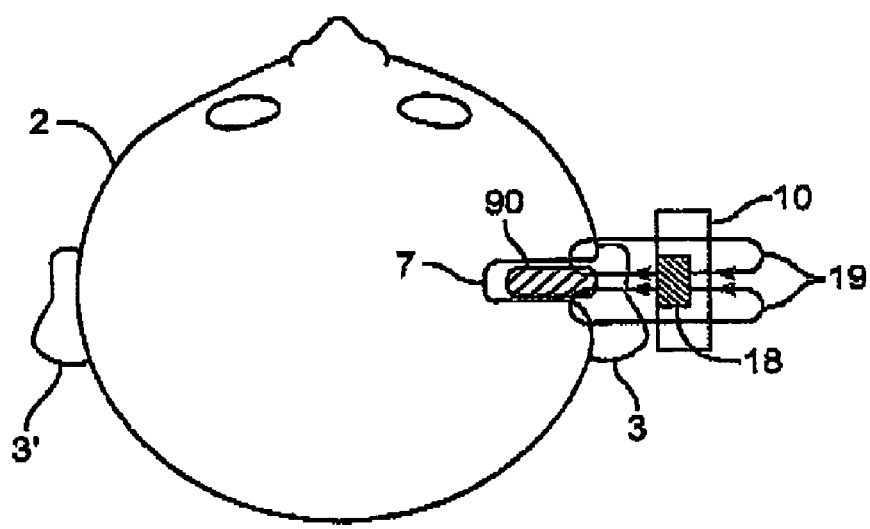
FIG. 12 is an embodiment of the hearing evaluation device incorporating a control magnet within its housing to remotely control the function of a hearing aid worn in the ear canal.
Figure 13:
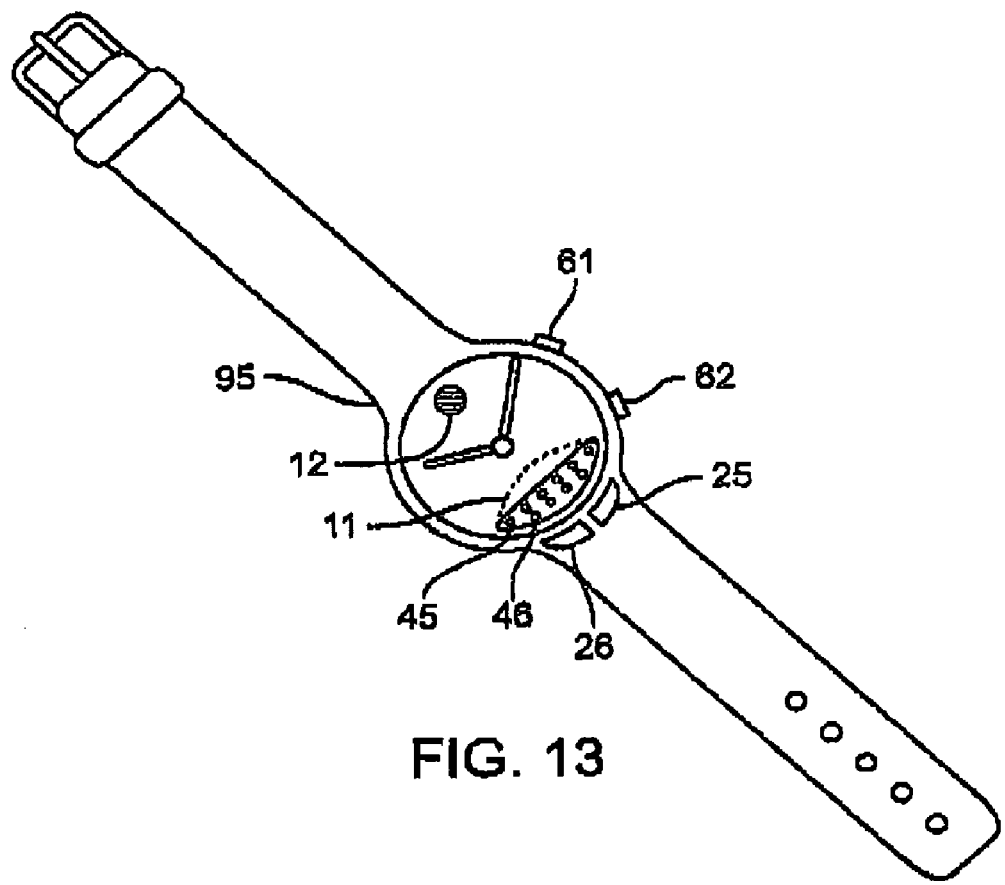
FIG. 13 is a view of an embodiment of the hearing evaluation device incorporated into a wrist watch.

FIG. 5 shows a block diagram of an exemplary embodiment of the personal hearing evaluation device 10. A controller 30 (i.e., microprocessor, microcontroller, etc.) is employed to perform various computational and control processes as will be described below. Memory 50 is employed to store program data (not shown) and test stimulus data (51 and 52) in digital format representative of acoustic test stimuli to be presented by the speaker 11 upon request by the test subject 1 or a test operator 8 (FIG. 11). Test stimulus data may be representative of speech words 51 (FIG. 5), noise 52 and any other signal which is of audiological significance (not shown) such as pure tone, warble tone, chirp, etc. Test stimulus data is retrievable from memory 50 by the controller 30 for conversion into analog signal 41 by the digital to analog (D/A) converter 40. The analog signal 41 is then delivered to a programmable volume control 42 and then to a power amplifier 43 for providing speaker input signal 44 to the speaker 11. Test sound 13 is finally produced by speaker 11 and directed towards the test subject 1 positioned in the direct sound field range as shown in FIG. 1.

The block diagram of FIG. 5 also shows position sensor 12 (an ultrasonic transducer) which transmits ultrasonic incident wave 14 and receives ultrasonic reflected wave 15 from the head or the ear of a test subject 1 (FIG. 1). The controller 30 is also connected to transmission circuitry 31 (labeled TRX circuitry in FIG. 5) and reception circuitry 32 (labeled RX circuitry in FIG. 5) for processing of signals sent and received during the process of position sensing. The microcontroller 30 is also connected to a switch array 60 (switches, keys, etc.) for selecting and presenting acoustic stimuli upon the request of a test subject 1 or a test operator 8 (FIG. 11).

A typical cycle for the position sensing process is automatic and begins when the controller 30 receives an actuation signal from a key (part of the switch array 60). The appropriate pattern of initial transmission signal 33 is produced by the controller 30 and fed into the transmission circuitry 31 which produces an output transmission signal 35 causing the position sensor 12 to transmit an ultrasonic incident wave 14 towards the head or ear of the test subject. A properly positioned head or ear with respect to the device will cause a reflected wave 15 to be received by the position sensor 12, which produces incoming reception signal 36. Reception circuitry 32 processes the incoming reception signal 36 and delivers a filtered reception signal 37 to controller 30. The latency period—the time between the onset of signal transmission and reception—is employed by the controller 30 to compute the position of head or ear with respect to the device 10. The above mentioned process is typically performed in repeated bursts or packets of sensing signals, according to an appropriate detection algorithm, for determining the correct position of the device in the presence of possible noise and interference.

Upon proper positioning of the device by the position sensor system (in FIG. 5 comprising ultrasonic transducer position sensor 12, transmission circuitry 31, reception circuitry 32 and microcontroller 30), the device 10 delivers an acoustic test stimuli via speaker 11 to the test subject 1. It will be understood, of course, that although the incident wave 14 delivered by position sensor 12 and the test stimulus delivered via speaker 11 to the test subject appear to be directed in opposite directions in the block diagram of FIG. 5, this is simply for the sake of convenience of block diagrammatic representation and they are actually delivered in the same general direction as indicated in FIGS. 1 and 2. The automatic position sensing process is relatively rapid and typically occurs within 100 milliseconds (ms) after pressing a stimulus request key. Therefore, the onset of a test stimulus is essentially perceived "instantaneously" by a test subject.

However, if the positioning of the head is determined improper by the position sensor system (i.e., out of range, improper orientation, reverberant environment, etc.), the device presents the appropriate alarm indicator to the user. FIG. 2 for example shows an alarm light indicator 71 in the form of an LED (light emitting diode). Alternatively, a LCD (liquid crystal display) or even distinct audible sounds (i.e., buzzer-like) may be employed to alert the user of an improper positioning or function of the invented device. Display elements are collectively shown as LED/Display 70 in FIG. 5.

The device in the embodiment shown in FIG. 5 also incorporates a microphone 16 for sensing the ambient background noise 17 and ensuring acceptable noise levels prior to delivering a test stimulus. For example, the onset of a test stimulus may be automatically delayed or canceled if the ambient noise level was measured to exceed the level of an intended test stimulus. In another example, the level of intended test stimulus may be automatically increased to ensure acceptable signal to noise (S/R) ratio. The microphone may also be used for self-testing or auto-calibration of the device by sensing a calibration signal (not shown) delivered by the speaker 11 and comparing its measured characteristics to a predetermined pattern stored in memory 50. The microphone signal 39 from the microphone 16 is amplified by microphone signal amplifier 38 and delivered to controller 30 for digital sensing and computation. An analog to digital converter (not shown) is preferably employed, within the microcontroller 30 or as a separate component within the device, in order to convert microphone signals and various analog signals within the device into a digital format for interpretation and computation by the controller 30. A battery 27 is provided to power the portable hearing evaluation device 10 of the present invention.

Figure 6:
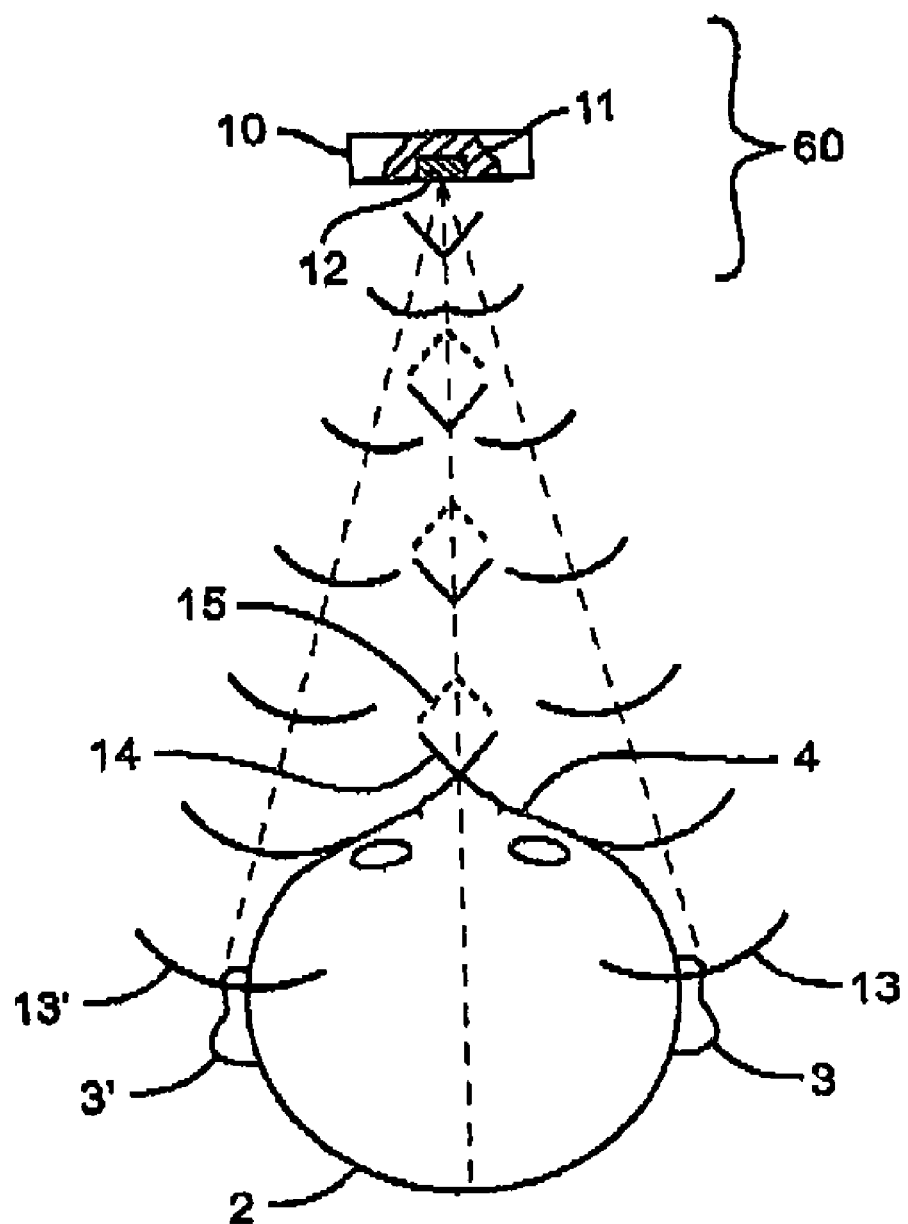
FIG. 6 is a view of the hearing evaluation device correctly positioned in range at 0° degree incidence angle with respect to the forehead of a user in a binaural test mode.

FIG. 6 shows an example of a binaural test mode of the hearing evaluator device 10 positioned within proper range 60 and orientation (0° degree incidence angle) with respect to the user's forehead 4. Sound, 13 and 13', from speaker 11 is directed at right 3 and left 3' ears, respectively. A sufficient portion of incidence wave 14 transmitted from position sensor 12 is reflected back (reflected wave 15) to the position sensor 12 causing reception signal 37 (FIG. 5) of sufficient strength and latency for proper detection by the position sensing system. The distance of the device with respect to the forehead is preferably in the range of 30–60 cm to accommodate the arm length range of individuals holding the device as shown in FIGS. 1 and 2.

Figure 7:
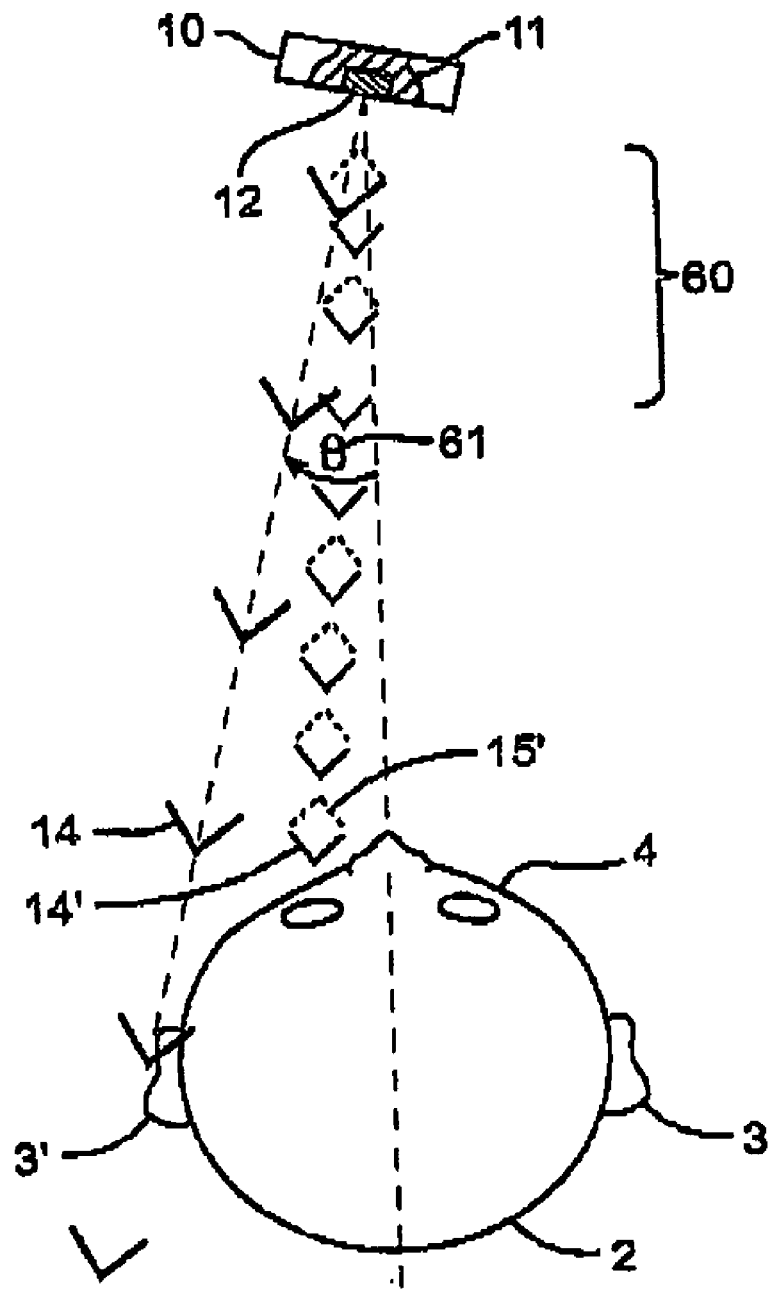
FIG. 7 is a view of the hearing evaluation device being incorrectly positioned out of range and oriented at an unacceptable incidence angle with respect to the forehead of a user in a binaural test mode.

FIG. 7 shows an example of a binaural test mode with device 10 being incorrectly positioned outside the proper range 60 and also being incorrectly oriented with respect to the forehead 4 of the user 1. Since the incident angle θ (61) is much greater than 0° degree, the incident wave is minimally reflected, if at all. However, even if a fringe incident wave 14' is reflected causing a fringe reflected wave 15', the reception signal 37 is insufficiently weak as determined by the position sensor system.

In the binaural test mode, shown in FIGS. 6 (correct) and 7 (incorrect), both ears are typically involved in the hearing evaluation process. However, if only a single ear is to be tested in this mode, the other ear must be excluded by an appropriate method such as by occluding the non-test ear or by turning off a hearing aid worn in the non-test ear.

Figure 8:
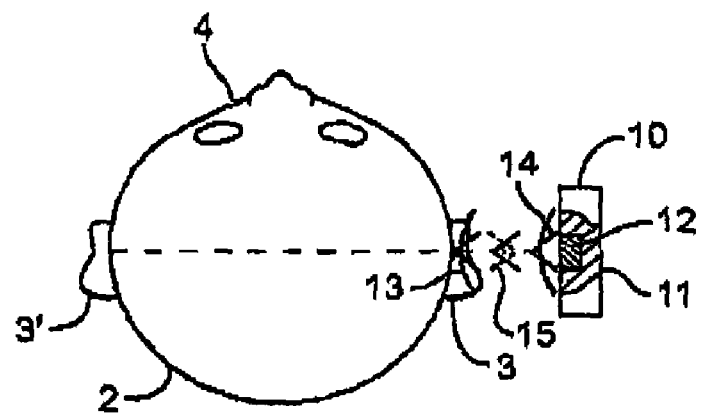
FIG. 8 is a view of the hearing evaluation device being correctly positioned at 0° degree incidence angle with respect to an ear of a user in a monaural test mode.
Figure 9:
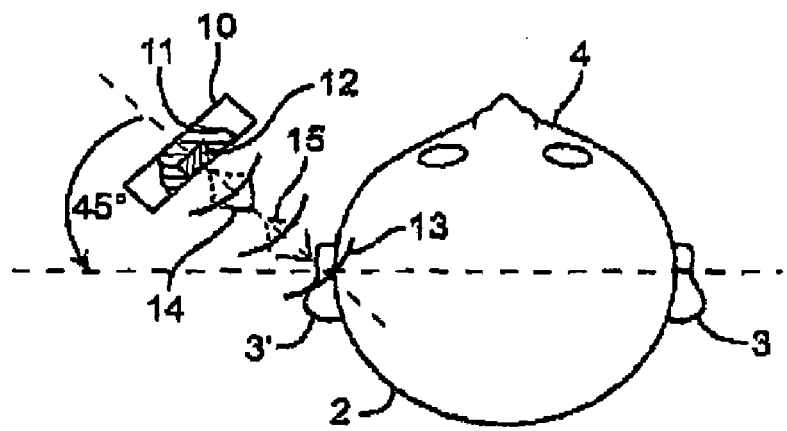
FIG. 9 is a view of the hearing evaluation device also being correctly positioned at 45° degree incidence angle with respect to an ear of a user in an alternate monaural test mode.

FIG. 8 shows a preferred method for monaural hearing evaluation. The invented device 10 is placed within exceptional proximity to a single test ear 3 (right). In this monaural test mode, the device is placed within a 2–10 cm range from the ear and oriented at incidence range of 0°–45° degrees. FIG. 8 shows device placement at 0° degree incidence with respect to right ear 3. FIG. 9 shows device placement at 45° degrees incidence with respect to a left ear 3'.

FIG. 2 shows a perspective view of an exemplary embodiment of the hearing evaluation device 10 being held by hand 5 of a test subject (1 in FIG. 1). The device 10 comprises a first key 61 configured for pressing by the thumb 6 and a second key 62 configured for pressing by the index finger 7. The speaker 11 is oriented towards one or both ears as shown in FIGS. 6–9 and described above. Light Emitting Diodes (LED), 71 and 72, are employed to provide visual indications to the test subject 1. For example, an alarm LED 71 (typically a red light) is provided to indicate incorrect positioning of the device. LED 72 (typically a green light) may be used to indicate valid "OK" operation or charged battery. A directional filter 21 is fitted over the position sensor 12 to improve the directionality of incident wave 14, reflected wave 15, or both. A speaker cover 45 with holes 46, or an acoustically transparent structure (not shown), are provided to protect the speaker 11 within while allowing test sound 13 to pass through towards the test subject.

FIG. 2 also shows a first switch 25 (two-position switch) for selecting one of two signal types; speech (marked SP) or narrow-band-noise (marked NBN). A second switch 26 (three-position switch) provides selection of one of three frequency bands; low, medium or high (labeled LF, MF and HF, respectively). Keys, 61 and 62, are employed to select at least two levels of sounds. In the preferred embodiment, these two keys present soft and comfortable sound levels, both with respect to normal hearing individuals. Soft sound key 62, for example, (marked "S") preferably presents a fixed level sound in the range of 20 to 40 dB HL (hearing level). Comfortable sound key 61, for example, (marked "C") preferably presents a fixed level sound in the range of 45 to 60 dB HL.

The exemplary key and switch configuration of the device 10 in FIG. 2 leads to a combination of 12 individual test stimuli (2 keys×2 positions×3 positions) for performing various hearing evaluation tests. The accuracy of each test stimuli presented is ensured and regulated by the position sensor system incorporated within as described above. For example, if the speaker-head distance is measured (automatically) to be at 50 cm (i.e., binaural test mode), the speaker input signal 44 (FIG. 5) is then automatically increased relative to a condition where the speaker-ear distance is at 5 cm (i.e., monaural test mode). This automatic adjustment (auto-calibration) is necessary in order to produce an equal perception of loudness at the ear, irrespective of the test mode or the exact position of the speaker 11.

In addition to the automatic level adjustment affecting the speaker input signal, the frequency characteristics of the test sound may also be manipulated in order to minimize inaccuracies associated with frequency-dependent stimulus. In pure tone test sounds, for example, it may be desirable to slightly shift the test frequency in order to minimize the affects 110 of standing waves. A slight shift in the frequency is considered acceptable in audiological standards for most audiometric evaluations. For example, ±1% and ±3% frequency variation is permissible for type 1 and type 4 audiometers, respectively, according to ANSI S3.6, 1996.

The types of test signals possible with the present invention are not limited to speech, pure tones or narrow-bandnoise. Virtually any signal of audiological significance may be reproduced from a digital recording, or synthesized, by the microcontroller for the presentation to the test subject. Other possible signal types include warbled tones, white noise, chirp (sine-wave composition), speech noise and other frequency weighted signals.

The hearing evaluator of the present invention, although miniature and employing a miniature audio transducer (speaker) 11, can produce sound at significant intensity levels when positioned within close proximity to a test ear as shown in FIGS. 8 and 9. In this monaural test mode, the intensity levels of test stimuli at the ear can reach 90 dB-SPL (sound pressure level) more while consuming little energy available from standard batteries. For example, a 98.3 dB-SPL tone at 4000 Hz. was produced at the ear from a miniature high fidelity speaker (model 4D06C manufactured by Panasonic) when positioned approximately 5 cm from an individual's ear (monaural test mode FIG. 8). The speaker input signal voltage to produce the 98.3 dB at 5 cm was measured at 0.7 Vrms. The power into the speaker measured at about 0.05 watt, which is readily available from standard batteries. Loud level sounds at 90 dB-SPL are particularly useful in assessing the aided hearing function of an individual during the fitting process to ensure comfortable hearing when the hearing aid is subjected to loud sounds. If found too loud by the aided test subject, the maximum output of the hearing aid must be reduced to a more acceptable level.

The same speaker input signal level (0.7 Vrms) produced only 82.5 dB-SPL at the ear when the speaker was positioned at 40 cm. Obviously, by scaling down the speaker input signal, soft and even threshold level sounds can be readily produced at virtually any distance within the preferred usable range of 2 to 60 cm. The above sound pressure level measurements at the ear were taken by probe-tube microphone system (model ER-7C, manufactured by Etymotic Research).

The personal hearing evaluator device 10 can be used by a test subject 1 to conduct a self-administered screening evaluation (pass/fail test) using the keys provided on the device.

The device in the above-described preferred and alternate embodiments can also be used in a professional setup during the fitting process of a hearing aid. For example, in the unaided condition and prior to hearing aid selection, the threshold of hearing of an individual (test subject) is determined at various audiometric frequencies. Later on, the hearing evaluation is performed while a hearing aid is in situ (worn in the ear or the ear canal). In this aided condition, adjustments to the in-situ hearing aid are made while the test subject responds to the sound field stimuli produced by the hand-held device of the present invention. For example, soft level gain, compression ratio, maximum output, frequency response, attack time and any other parameter of a hearing aid, may be adjusted based on the test sounds produced from the speaker of the hand-held device. Following the fitting process, the test subject can use the hearing evaluation device 10 as a personal hearing evaluator. For example the acuity of the aided hearing can be checked regularly by the user at home by pressing the soft level key (62 in FIG. 2) to present soft level sounds (audible by normal hearing individuals). This is important because hearing aids tend to gradually deteriorate with time due to moisture or earwax contamination. A regular check-up by the hearing evaluation device of the invention should detect possible changes in either the hearing aid or the hearing ability of the user.

Figure 10:
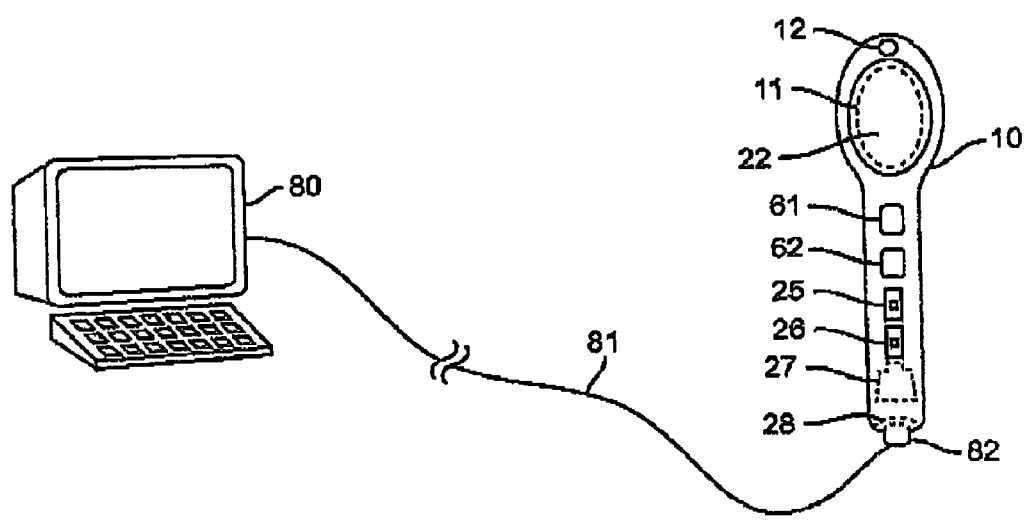
FIG. 10 is a view of the hearing evaluation device of the present invention connected to an auxiliary instrument.

In the above-described embodiments, the hand-held hearing evaluation device is described in stand-alone configurations for use in unaided or aided conditions. FIG. 10 shows an alternate embodiment of the device 10 connected to an auxiliary instrument 80 (shown as a computer or computer-based instrument). The elongated hand-held device 10 is provided with an interface port 28 (also shown in FIGS. 2 and 5) for connecting to auxiliary instrument 80 via the connection cable 81 and its electrical plug 82 inserted into interface port 28 of the device 10. The auxiliary instrument 80 is used by a test operator to control the device 10 by sending the appropriate control commands to the controller 30 (FIG. 5) of the device via auxiliary interface circuitry 48 (FIG. 5). This auxiliary control mode available by the present invention allows a test operator (other than the test subject holding the device 10) to remotely control the function of the device 10. One advantage of this mode is to allow the operator to select a test stimulus from a broader range than possible with the device in its stand-alone configuration (having relatively a limited number of key and switch selection). The remote control interface mode is useful, for example, in performing a more comprehensive hearing evaluation such as for conducting a complete audiogram test involving 6 or more frequencies. In the remote control mode by an auxiliary instrument 80, a key (such as key 61 or key 62) within the device 10 can be used as a response key to register responses of the test subject and relay such registration to auxiliary instrument 80 when the test subject hears and presses the response key.

The auxiliary instrument 80, in conjunction with a response key on the device, can be used to automate the presentation of a hearing test according to procedures and protocols known in the field of automated audiometry. Furthermore, the auxiliary instrument 80 may be used to program the connected device 10 to perform specific test or function according to the needs of the individual test subject. The auxiliary instrument 80 may be a computer as shown, a microprocessor-based audiometer instrument (not shown), or any other suitable control instrument. The connection between the auxiliary instrument 80 and the device 10 may be via a direct wire as shown in FIG. 10, or via a wireless connection (not shown) as widely known in the field of wireless control and communications.

The auxiliary instrument mode is ideally suited during the initial fitting evaluation at the site of the hearing aid dispensing professional. For example, a test operator (audiologist, doctor, nurse, etc.) can perform various unaided and aided evaluation on a test subject holding the device by hand. Once the hearing aid fitting process is completed, the hand-held device 10 is then disconnected from the auxiliary instrument 80 and offered to the test subject as a personal evaluator. Similarly, the personal evaluator device 10 can be used to regularly verify the proper function of an in-situ hearing device. The personal evaluator device 10 comprises a battery 27 for powering the device in its stand-alone mode after being disconnected from the auxiliary instrument 80.

The auxiliary instrument mode is also suited for remotely administering a hearing test when the subject is remotely present and the device is connected to the appropriate network. For example, a hand-held device 10 can be directly connected to a computer which is also connected to a remote computer (auxiliary instrument) via the Internet. This way, a hearing professional can remotely administer a test to a test subject, present at home for example. In this case, the test subject simply connects the hearing evaluation device 10 to a computer port (not shown) of a personal computer connected via the Internet to the computer of the hearing professional. Other remote interface methods are possible and conceivable as will become obvious to those skilled in the art of computers, communications and networking.

The invented device 10 is highly portable and configured for easy transport and convenient hand-held operation as described in the above embodiments. For example, the device in FIG. 2 is shown resembling a hand-held stopwatch or a garage-door opener. In FIG. 10 the device 10 is shown resembling a pen. Other designs, well within the scope of this invention, include wristwatch 95 (FIG. 13) and other configurations, which will become obvious to those skilled in the art of miniature personal instrument design.

The invented device 10, although most suitable for holding by a test subject who orients the speaker towards his or her own ears, it may be desirable in certain conditions for a test operator (a hearing professional, parent, spouse, etc.) to hold the device 10 and assist in conducting a hearing test. This may be necessary for testing young children, persons with poor dexterity, and other difficult to test individuals. FIG. 11 shows a test operator 8 holding the hearing evaluation device 10. Similarly, the test sound 13 and the incident wave 14 of the position sensor 12 are directed towards the head 3 of the test subject 1 to properly deliver acoustic test stimuli to one or both ears of the test subject 1.

The personal hearing evaluator may incorporate wireless remote control means for remotely controlling or programming a hearing aid. For example, hearing aid volume can be remotely adjusted, or the power may be remotely turned on or off Wireless control means are widely known in the field of hearing aids and include ultrasonic, electromagnetic, sonic, magnetic and infrared signals. In a preferred embodiment shown in FIG. 12, the hearing evaluator device 10 comprises a magnet 18 having a magnetic field 19 which remotely, but within close proximity, controls a hearing aid 90 positioned in the ear canal 7. The magnetic field 19 may be reversed in its direction (not shown) simply by flipping the device and thus reversing the polarity of the magnet 18 within. The details of such magnetic control operation are disclosed in a pending patent application Ser. No. 09/181,533 of the same inventor, filed Oct. 28, 1999 and incorporated herein by reference. The magnet typically employed within a speaker 11 transducer may be relied on for such remote control application thus eliminating the need for an additional magnet.

The position sensor system in the preferred embodiments, described above, employ ultrasonic transconduction for sending and receiving ultrasonic waves. However, other contactless position sensing means are possible and may be equally suitable as known by those skilled in the art of proximity and position sensing. For example by employing optical transducers (i.e., infrared LED) in conjunction with appropriate directional optical filters. In another example, a sonic wave produced by the speaker 11 may be utilized for position sensing.

Although a presently contemplated best mode of practicing the invention has been described herein with reference to certain presently preferred and alternate embodiments and methods of use, it will be recognized by those skilled in the art to which the invention pertains from a consideration of the foregoing description, that variations and modifications of these exemplary embodiments and methods may be made without departing from the true spirit and scope of the invention. Thus, the above described embodiments of the invention should not be viewed as exhaustive or as limiting the invention to the precise configurations or techniques disclosed. Rather, it is intended that the invention shall be limited only by the appended claims and the rules and principles of applicable law.

What is claimed is:

1. A hand held device for performing sound field hearing testing, said device comprising:
    a housing configured to be held in the hand of a user;
    an audio transducer disposed on or within the housing, the transducer configured to produce acoustic test stimuli to a test subject within a direct sound field range of the audio transducer;
    a contactless position sensor system configured to remotely measure a distance of said device with respect to the head or part thereof of said test subject; and
    means for adjusting characteristics of said acoustic stimuli responsive to the position sensor system, the adjustment means configured to produce a substantially constant acoustical perception at the subject's ear irrespective of device position or test mode.

2. The device of claim 1, wherein the adjusting means is configured to adjust the acoustic stimuli responsive to ambient noise.

3. The device of claim 1, wherein said device is configured as a wrist watch.

4. The device of claim 1, wherein said device is configured for operation by a test operator assisting said test subject.

5. The device of claim 1, including means for performing said hearing evaluation in an unaided condition in which said test subject is not wearing a hearing aid.

6. The device of claim 1, including means for performing said hearing evaluation in an aided condition in which said test subject is wearing a hearing aid.

7. The device of claim 6, including means for performing said hearing evaluation in said aided condition to verify functionality of said hearing aid worn by said test subject.

8. The device of claim 6, including means for performing said hearing evaluation in said aided condition to adjust at least one parameter of said hearing aid.

9. The device of claim 1, further comprising means for delivering at least one of said acoustic test stimuli within the soft level listening range of normal hearing individuals.

10. The device of claim 9, wherein said soft level listening range is between 20 and 40 dB HL.

11. The device of claim 1, further comprising means for delivering at least one of said acoustic test stimuli within the comfortable level listening range of normal hearing individuals.

12. The device of claim 11, wherein said comfortable level listening range is between 45 and 65 dB HL.

13. The device of claim 1, wherein said contactless position sensor system comprises at least one of an optical transducer, acoustic transducer and ultrasonic transducer.

14. The device of claim 1, wherein said contactless position sensor system comprises means for determining if the device is within an operable range and orientation with respect to the head or part thereof of said test subject.

15. The device of claim 1, wherein said contactless position sensor system comprises a transmitting transducer and a receiving transducer.

16. The device of claim 15, wherein said contactless position sensor system comprises means for computing the distance between the device and the head or said part thereof of said test subject based on the latency period between a transmitted signal emitted by said transmitting transducer and reflected signal received by said receiving transducer.

17. The device of claim 15, wherein said transmitting transducer and receiving transducer are combined in a unitary bidirectional transducer.

18. The device of claim 1, further comprising means to select from at least two types of acoustic test stimuli including speech, noise and tone types.

19. The device of claim 1, further comprising means to select acoustic test stimuli in at least two frequency ranges.

20. The device of claim 1, further comprising at least one switch for selection of at least one acoustic test stimulus.

21. The device of claim 1, further comprising interface means for connecting a remote instrument to said device for remotely operating said device.

22. The device of claim 21, wherein said remote instrument comprises a computer.

23. The device of claim 21, wherein said interface means comprise an electrical cable.

24. The device of claim 21, wherein said interface means comprise the Internet.

25. The device of claim 21, wherein said interface means comprise a wireless link.

26. The device of claim 21, further comprising response registration means for registering test responses by said test subject.

27. The device of claim 1, further comprising visual display means, including liquid crystal display (LCD) and light emitting diode (LED).

28. The device of claim 1, further comprising a controller.

29. The device of claim 1, further comprising memory for storage of data representative of acoustic test stimuli.

30. The device of claim 1, further comprising a microphone.

31. The device of claim 30, wherein said microphone provides means for measuring ambient background noise.

32. The device of claim 6, further comprising wireless remote control means for controlling or adjusting at least one parameter of said hearing aid worn by said test subject.

33. The device of claim 32, wherein said wireless remote control means comprise a magnet.

34. A hand held device for performing sound field hearing evaluation in a contactless manner with respect to a test ear of a test subject, said device comprising:
- a housing configured to be held in the hand of a user and direct sound and a position sensing signal at a user's head or a head of anther test subject;
- an audio transducer for delivering acoustic test stimuli to said test subject holding said device within a direct sound field range of said audio transducer, the transducer disposed on or within the housing;
- means for selecting delivery of said acoustic test stimuli through said audio transducer at two or more intensity levels for performing one or more supra-threshold hearing measurements, and
- means for selecting delivery of said acoustic test stimuli through said audio transducer in at least two frequency ranges for performing hearing evaluation in at least two frequency ranges; and
- a wireless position sensor system for remotely measuring the distance of said device relative to the head or portion of the head of the test subject,
- means for adjusting characteristics of said acoustic test stimuli in responsive to the position sensor system, the adjustment means configured to produce a substantially constant acoustical perception at the subject's ear irrespective of device position or test mode.

35. The hand held device of claim 34, wherein said device is configured for operation by said test subject.

36. The hand held device of claim 34, wherein said device is configured for operation by a test operator assisting said test subject.

37. The hand held device of claim 34, including means for performing said hearing evaluation in an unaided condition in which said test subject is not wearing a hearing aid.

38. The hand held device of claim 34, including means for performing said hearing evaluation in an aided condition in which said test subject is wearing a hearing aid.

39. The hand held device of claim 34, further comprising a contactless position sensor system for measuring the position of said device with respect to the head or part thereof of said test subject.

40. The hand held device of claim 39, further including means for adjusting the characteristics of said acoustic test stimuli, in response to position measurements performed by said contactless position sensor system.

41. The hand held device of claim 39, wherein said contactless position sensor system comprises an ultrasonic transducer.

42. The hand held device of claim 34, further comprising means to select from at least two types of said acoustic test stimuli including speech, noise and tone types.

43. The hand held device of claim 34, further comprising interface means for connecting a remote instrument for remotely operating said hand held device.

44. The hand held device of claim 43, wherein said remote instrument comprises a computer.

45. The hand held device of claim 43, wherein said interface means comprise the Internet.

46. The hand held device of claim 43, further comprising response registration means for registering test responses by said test subject.

47. The hand held device of claim 34, further comprising visual display means, including an liquid crystal display (LCD) and light emitting diode (LED).

48. The hand held device of claim 34, further comprising a microphone.

49. The hand held device of claim 48, wherein said microphone provides means for measuring ambient background noise.

50. A system for performing hearing evaluation of a test subject comprising:
a) a hand held device containing an audio transducer within, said hand held device being positionable within a direct sound field range of said audio transducer with respect to a test ear of the subject while held in a hand of the subject so as to conduct a hearing test in a contactless manner with respect to the test ear of said test subject;
b) an auxiliary instrument operably connected to said hand held device for remotely controlling the operation of said hand held device;
c) means for selecting the delivery of acoustic test stimuli through said audio transducer at two or more intensity levels and at two or more frequency ranges;
d) a contactless position sensor system for remotely measuring the distance of said device relative to the head or portion of the head of the test subject the sensor system configured to be operarable in a packet signaling sensing mode to compensate for interference; and
e) means for adjusting said acoustic stimuli based on distance measured by said position sensor the adjusting means configured to produce substantially equal acoustical perceptions at the subject's ear irrespective of the measured distance.

51. The system of claim 50, wherein said hand held device is independently operable as a hearing evaluator when detached from said auxiliary instrument.

52. The system of claim 50, including means for performing said hearing evaluation in an unaided condition in which said test subject is not wearing a hearing aid.

53. The system of claim 50, including means for performing said hearing evaluation in an aided condition in which said test subject is wearing a hearing aid.

54. The system of claim 50, wherein said auxiliary instrument is a computer.

55. The system of claim 50, including means for remotely connecting said auxiliary instrument to said hand held device through the Internet.

56. A method of evaluating a test subject's hearing with a hand held device containing a contactless position sensor system and an audio transducer, said method comprising:
   a) measuring the distance of said subject's head or part thereof relative to said device with said position sensor system when said device is oriented toward said subject's head or part thereof;
   b) adjusting a characteristic of acoustic test stimuli utilizing the distance measurement to produce a substantially constant acoustical perception at the subject's ear irrespective of the measured distance; and
   c) delivering said acoustic test stimuli to said test subject while said device is oriented toward said subject's head or part thereof of interest.

57. The method of claim 56, including orienting said audio transducer at approximately 0° incidence and within a distance range of 30–60 cm with respect to the forehead of said test subject, while performing said step of delivering acoustic test stimuli.

58. The method of claim 56, including orienting said audio transducer at approximately 0°–45° incidence range and within a distance range of 2–10 cm with respect to a test ear of said test subject while performing said step of delivering acoustic test stimuli, for monaural hearing evaluations.

59. The method of claim 56, including delivering said acoustic test stimuli in an unaided condition in which said test subject is not wearing a hearing aid.

60. The method of claim 56, including delivering said acoustic test stimuli in an aided condition in which said test subject is wearing a hearing aid.

61. The method of claim 60, including delivering said acoustic test stimuli in said aided condition to verify the functionality of said hearing aid.

62. The method of claim 60, including delivering said acoustic test stimuli in said aided condition to adjust at least one parameter of said hearing aid.

63. The method of claim 56, including connecting a remote instrument to said device via an interface to remotely control said device during said hearing evaluation.

64. The method of claim 63, including connecting said remote instrument to said device via the Internet.

65. The method of claim 63, wherein said remote instrument is a computer.

66. The method of claim 63, wherein said remote instrument is an audiometer.

67. A method of hearing evaluation for an individual holding a hand held device containing an audio transducer for delivering acoustic test stimuli in a contactless manner and within a direct sound field range of said audio transducer with respect to a test ear of said individual, said method comprising:
   a) performing position sensing to remotely measure a distance of said individual relative to said device;
   b) calibrating said acoustic test stimuli based on the distance measured by said position sensing so as to produce a substantially constant acoustical perception at the test ear irrespective of the measured distance;
   c) delivering at least two levels of said acoustic test stimuli to said test ear of the individual; and
   d) delivering said acoustic test stimuli in at least two frequency ranges.

68. The method of claim 67, including orienting said audio transducer at approximately 0° incidence and within a distance range of 30–60 cm with respect to the forehead of said individual.

69. The method of claim 67, including orienting said audio transducer at approximately 0°–45° incidence range and within a distance range of 2–10 cm with respect to said test ear, for monaural hearing evaluations.

70. The method of claim 67, including performing said hearing evaluation in an unaided condition in which said individual is not wearing a hearing aid.

71. The method of claim 67, including performing said hearing evaluation in an aided condition in which said individual is wearing a hearing aid.

72. The method of claim 67, including connecting a remote instrument to said device via an interface to remotely control said device during said hearing evaluation.

73. The method of claim 72, including connecting said remote instrument to said device via the Internet.

74. The method of claim 72, wherein said remote instrument is a computer.

* * * * *